United States Patent
Grant et al.

(10) Patent No.: US 9,212,946 B2
(45) Date of Patent: Dec. 15, 2015

(54) CAMPBELL DIAGRAM DISPLAYS AND METHODS AND SYSTEMS FOR IMPLEMENTING SAME

(75) Inventors: John Wesley Grant, Gardnerville, NV (US); Charles T. Hatch, Gardnerville, NV (US)

(73) Assignee: General Electric Company, Schenectady, NY (US)

( * ) Notice: Subject to any disclaimer, the term of this patent is extended or adjusted under 35 U.S.C. 154(b) by 825 days.

(21) Appl. No.: 13/492,435

(22) Filed: Jun. 8, 2012

(65) Prior Publication Data

US 2013/0328901 A1   Dec. 12, 2013

(51) Int. Cl.
*G01R 13/00* (2006.01)
*G01H 1/00* (2006.01)
*G01H 1/10* (2006.01)
*G01N 29/14* (2006.01)
*G01N 29/46* (2006.01)

(52) U.S. Cl.
CPC ............... *G01H 1/003* (2013.01); *G01H 1/00* (2013.01); *G01H 1/10* (2013.01); *G01N 29/14* (2013.01); *G01N 29/46* (2013.01); *G01N 2291/014* (2013.01)

(58) Field of Classification Search
CPC .......... G01H 1/00; G01H 1/003; G01H 1/10; G01N 29/14; G01N 29/46; G01N 2291/014
USPC ................ 702/66; 345/589; 73/660
See application file for complete search history.

(56) References Cited

U.S. PATENT DOCUMENTS

| | | | | |
|---|---|---|---|---|
| 4,996,880 | A * | 3/1991 | Leon et al. | 73/660 |
| 6,474,166 | B1 * | 11/2002 | Osawa et al. | 73/660 |
| 6,827,551 | B1 * | 12/2004 | Duffy et al. | 415/119 |
| 2010/0161285 | A1 * | 6/2010 | Egan | 702/191 |
| 2010/0262401 | A1 * | 10/2010 | Pfeifer et al. | 702/182 |
| 2011/0173006 | A1 * | 7/2011 | Nagel et al. | 704/500 |

OTHER PUBLICATIONS

Nelson, Dr. Frederick, Rotor Dynamics without Equations, International Journal of COMADEM, 10(3), Jul. 2007, pp. 2-10.

* cited by examiner

*Primary Examiner* — John Breene
*Assistant Examiner* — Eyob Hagos
(74) *Attorney, Agent, or Firm* — Fletcher Yoder, P.C.

(57) ABSTRACT

Methods and systems for creating Campbell diagram displays for illustrating vibration characteristics of a moving apparatus, such as a rotary machine, are provided. Data, representing vibration amplitudes and frequencies are recorded against rotational speeds of an apparatus. The data is used to create waveforms representing the forward and/or reverse vibration frequencies of the apparatus. The waveforms in turn are used to create spectral line envelopes to provide enhanced two dimensional images indicating the amplitudes of the vibrations of the apparatus at particular rotational speeds. The spectral line envelopes may be empty, filled with one or more colors, or other illustration features to impart solidity to the envelopes to enhance visibility.

15 Claims, 10 Drawing Sheets

CAMPBELL DIAGRAM DISPLAYS AND METHODS AND SYSTEMS FOR IMPLEMENTING SAME

BACKGROUND OF THE INVENTION

The present invention relates generally to instrumentation displays, and more specifically, to displays used in testing, monitoring and manufacturing equipment.

Campbell diagrams are used to illustrate a set of spectra obtained during startup or shutdown of a rotating machine, such as a turbine. A Campbell diagram may illustrate experimentally measured vibration response spectra as a function of the shaft rotational speed of the apparatus being tested.

Known Campbell diagrams present information in different formats. Some known diagrams employ color-coded, high density spectral data. Other diagrams employ circles to represent spectral amplitudes. Still other diagrams plot frequencies only along order line diagonals. Still yet other diagrams employ slanting diagonal lines, the lengths of which represent spectral amplitudes. Each of these methods represent attempts to present complex data in a compact form, which often requires a tradeoff between visual interest level or appeal, and substantive content.

However, known Campbell diagrams often suffer from data density issues, in that the creators of the Campbell diagrams attempt to illustrate too much data in the diagram. Furthermore, known Campbell diagrams frequently employ illustration techniques and conventions that result in diagrams that are visually noisy and difficult to interpret.

It would be desirable to provide a Campbell diagram display system and method that enables vibration spectra for rotary machines to be illustrated in a visually clean, yet content-filled manner.

BRIEF DESCRIPTION OF THE INVENTION

In an aspect, a method for indicating characteristics of a moving apparatus in the form of a Campbell diagram is provided. The method comprises measuring and recording with a control apparatus waveform data corresponding to amplitudes and frequencies of vibrations of the apparatus at each of a plurality of rotational speeds. The method further comprises processing the amplitude and vibration waveform data to create at least one spectral line representing the measured and recorded amplitudes and frequencies of the vibrations of the apparatus corresponding to a predefined rotational speed of the apparatus. The method further comprises generating a spectral line envelope from the at least one spectral line. The method further comprises plotting the spectral line envelope into a Campbell diagram representing rotational vibration characteristics for the apparatus. The method further comprises filling the spectral line envelope to create a visually solid two-dimensional image representative of amplitudes of vibration of the apparatus across a range of vibration frequencies at the predefined rotational speed of the apparatus.

In another aspect, a system for displaying characteristics of a moving apparatus in the form of a Campbell diagram is provided. The system comprises a control apparatus configured to measure and record waveform data corresponding to amplitudes and frequencies of vibrations of the apparatus at each of a plurality of rotational speeds. The control apparatus is further configured to process the amplitude and vibration waveform data to create at least one spectral line representing the measured and recorded amplitudes and frequencies of the vibrations of the apparatus corresponding to a predefined rotational speed of the apparatus. The control apparatus is further configured to generate a spectral line envelope from the at least one spectral line. The control apparatus is further configured to plot the spectral line envelope into a Campbell diagram representing rotational vibration characteristics for the apparatus. The control apparatus is further configured to fill the spectral line envelope to create a visually solid two-dimensional image representative of amplitudes of vibration of the apparatus across a range of vibration frequencies at the predefined rotational speed of the apparatus. The system further comprises a display apparatus configured to display the image of the Campbell diagram.

DETAILED DESCRIPTION OF THE INVENTION

Although specific features of various embodiments of the invention may be shown in some drawings and not in others, this is for convenience only. In accordance with the principles of the invention, any feature of a drawing may be referenced and/or claimed in combination with any feature of any other drawing.

Figure 1:
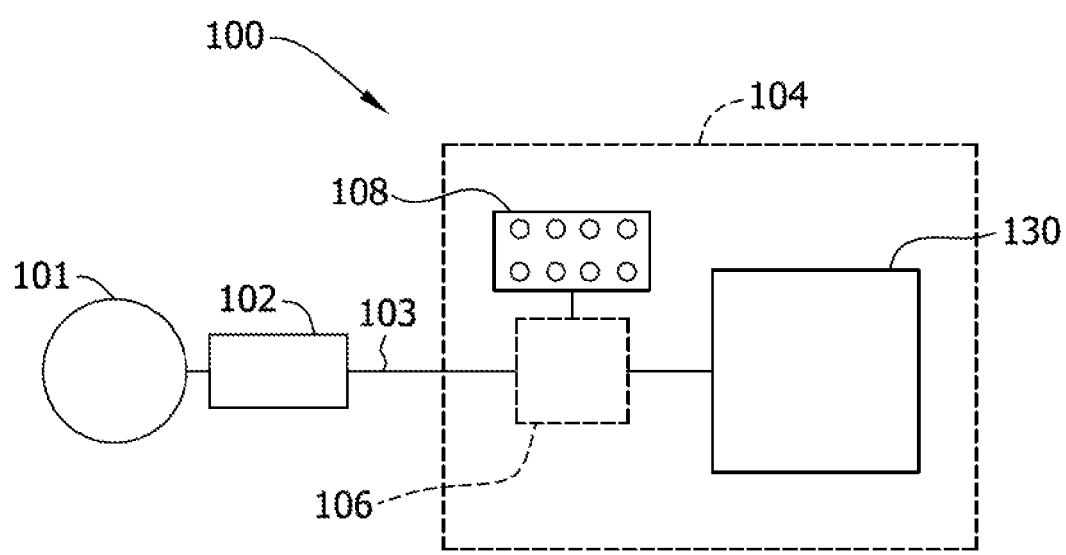
FIG. 1 is a schematic illustration of an exemplary measurement system that incorporates exemplary embodiments of Campbell diagram displays.

FIG. 1 is a schematic illustration of an exemplary measurement system 100 that may present a display 130, which may present exemplary embodiments of the Campbell diagrams of the present disclosure. The Campbell diagrams may be provided as part of a display system, which, in turn, may be incorporated into an overall equipment control system, wherein "equipment control system" should be understood to include not only systems which actually regulate the operation of devices or machinery, but also systems such as monitoring or measurement systems, such as the measurement system 100 illustrated in FIG. 1. For example, measurement system 100 may include one or more sensors 102, connected to an apparatus 101 being tested (such as a shaft or mounting structure of a rotary machine), that are likewise connected to a display system 104 that supports and provides display 130. Display system 104 may include one or more processors 106 that are configured to receive the raw signal(s) 103 being supplied by sensor(s) 102. In the exemplary embodiment, control panel 108 enables a user to selectively configure the Campbell diagram image 132 being shown on, e.g., display 130, shown in FIG. 4 (or any of the other displays shown and/or described herein), and select which numerical values processor(s) 106 derive from raw signal(s) 103 being transmitted from sensor(s) 102. Display system 104 may, for example, be a suitably programmed desktop or laptop computer, in which the internal processors of the desktop or laptop computer serve as processor(s) 106, its keyboard functions as control panel 108 and the screen of the desktop or laptop computer will show display 130.

As used herein, the term processor is not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Figure 2:
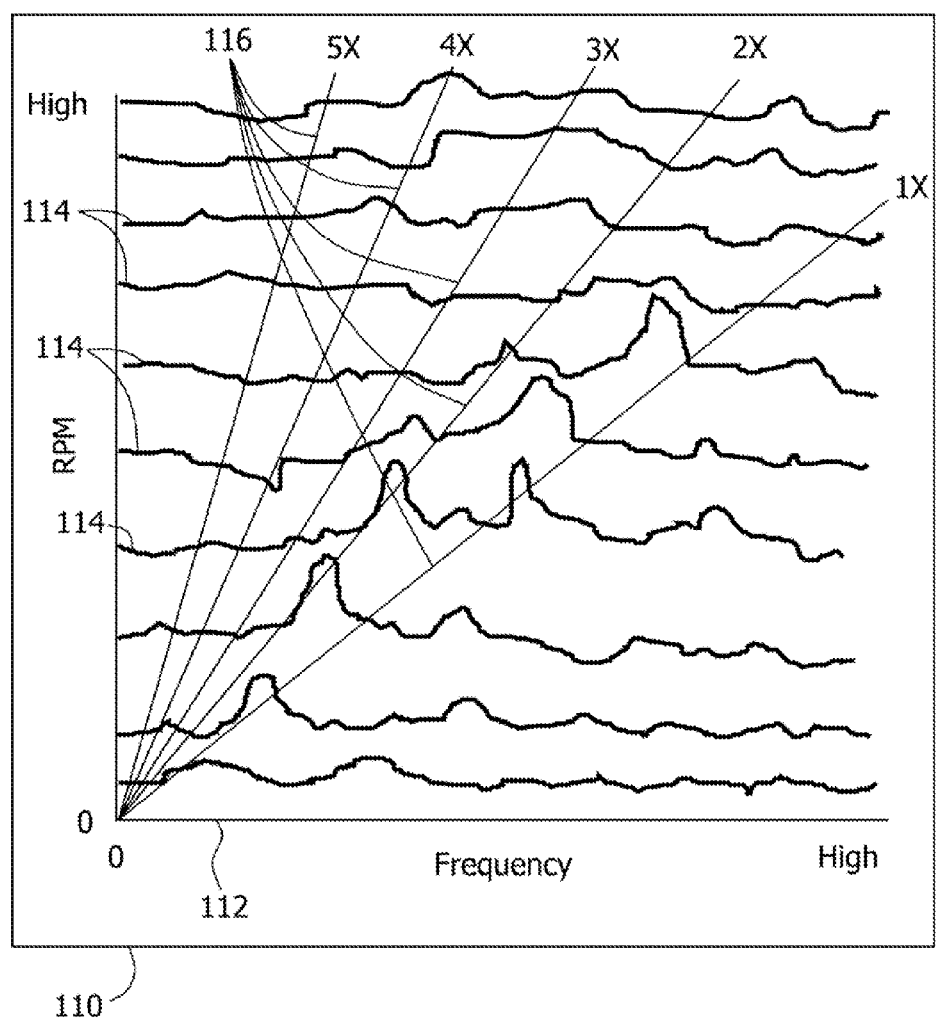
FIG. 2 is an illustration of a conventional display incorporating a cascade plot.
Figure 3:
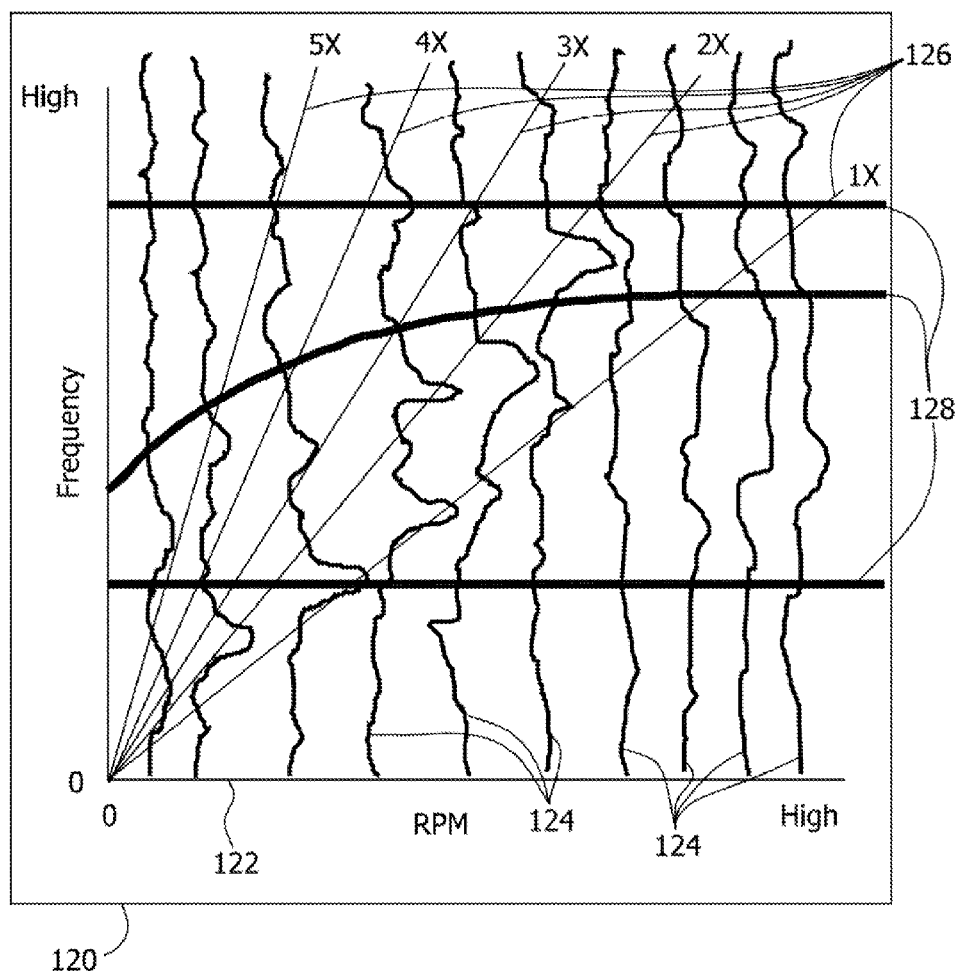
FIG. 3 is an illustration of a conventional Campbell diagram display.

FIGS. 2 and 3 illustrate conventional displays 110, 120, incorporating conventional cascade plot 112 and conventional Campbell diagram 122, respectively.

Cascade plot 112 (also sometimes known as a "waterfall" plot, spectrogram, or cumulative spectral decay plot) is a two-dimensional representation of a three-dimensional plot, used to show how two-dimensional information changes over time or some other variable. In the environment of rotary machines, in FIG. 2, the generally horizontal lines 114 represent the amplitude of vibrations (the heights of the "peaks") plotted against RPM (revolutions per minute) of the rotary device being tested, versus the frequency of the vibrations at the indicated rotational speeds. Diagonal lines 116 are "order" lines, which represent excitation frequencies as multiples of the rotational speed being measured. Lines 114 are plotted as an indication of vibration frequency and amplitude as the direct result of measurement sensors (not shown) connected to the rotary device being tested. Order lines 116 are calculated lines that are superimposed over lines 114.

To obtain Campbell diagram 122 of display 120 (shown in FIG. 3), cascade plot 112 is rotated ninety degrees(90°), and flipped, so that rotational speed (RPM) becomes the x-axis and vibration frequency (typically measured in Hertz-Hz) becomes the y-axis. Lines 124 continue to represent amplitude of vibrations at the indicated rotational speeds, and order lines 126 likewise continue to represent excitation frequencies as multiples of the rotational speed being measured. Again, lines 124 represent vibration frequency and amplitude plotted from direct measurement, while lines 126 are calculated and superimposed over the plot. Additionally superimposed on display 120 are modal natural frequency lines 128, representing frequencies at which resonance (amplified vibration) may occur. Notably, lines 128 generally follow points of intersection of lines 124 and 126.

Figure 4:
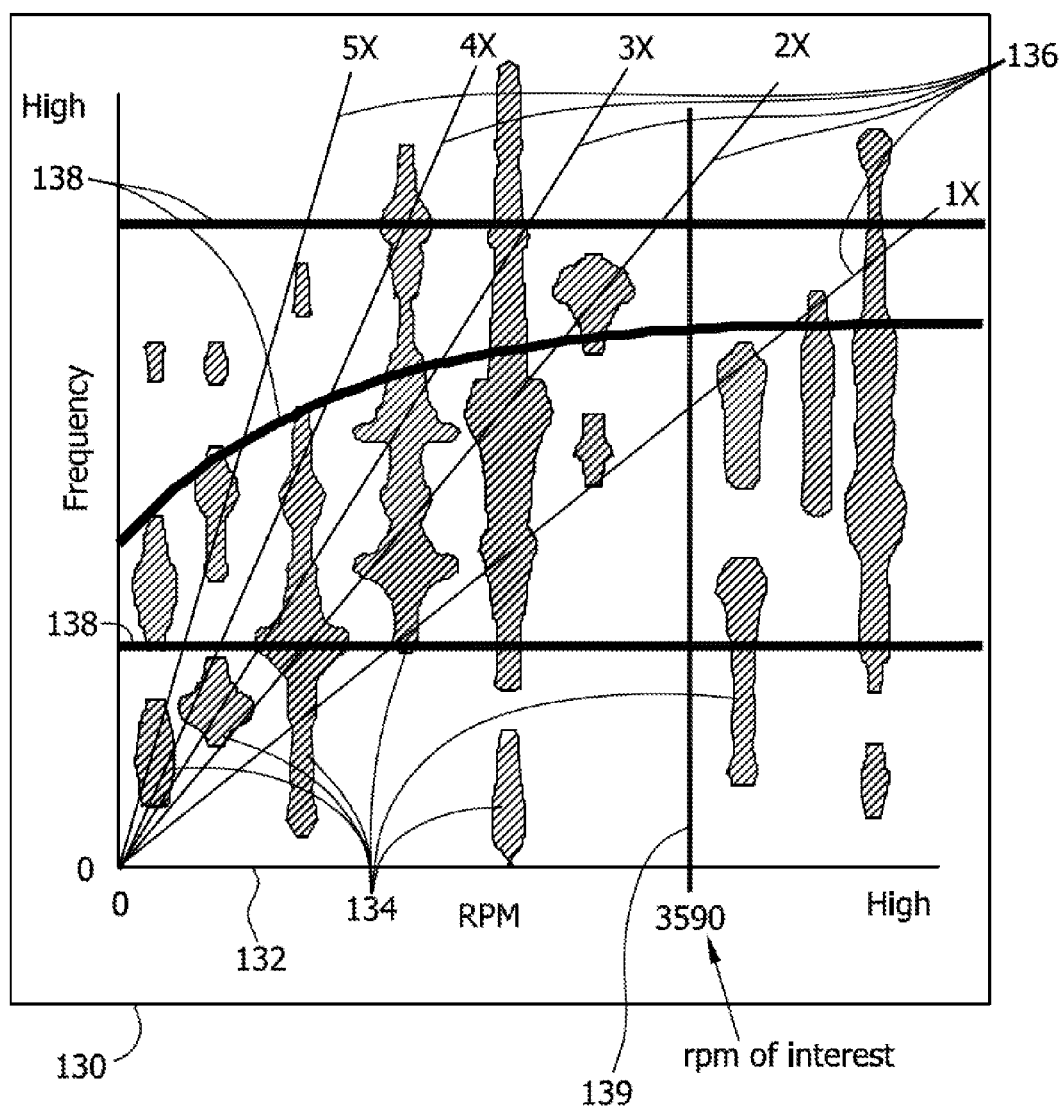
FIG. 4 is an illustration of an exemplary Campbell diagram display.

FIG. 4 is an illustration of exemplary Campbell diagram display 130 showing Campbell diagram 132. Order lines 136 and modal natural frequency lines 138 are sensed and/or calculated and plotted in the same manner as corresponding lines 126 and 128 of the Campbell diagram 122 of FIG. 3. Vibration frequency/amplitude spectral line pairs 134 are plotted as filled envelopes mirrored about the particular RPM values at which the frequencies and amplitudes were measured, thus providing an enhanced view and appreciation for the magnitudes of the vibrations of interest.

Figure 5A:
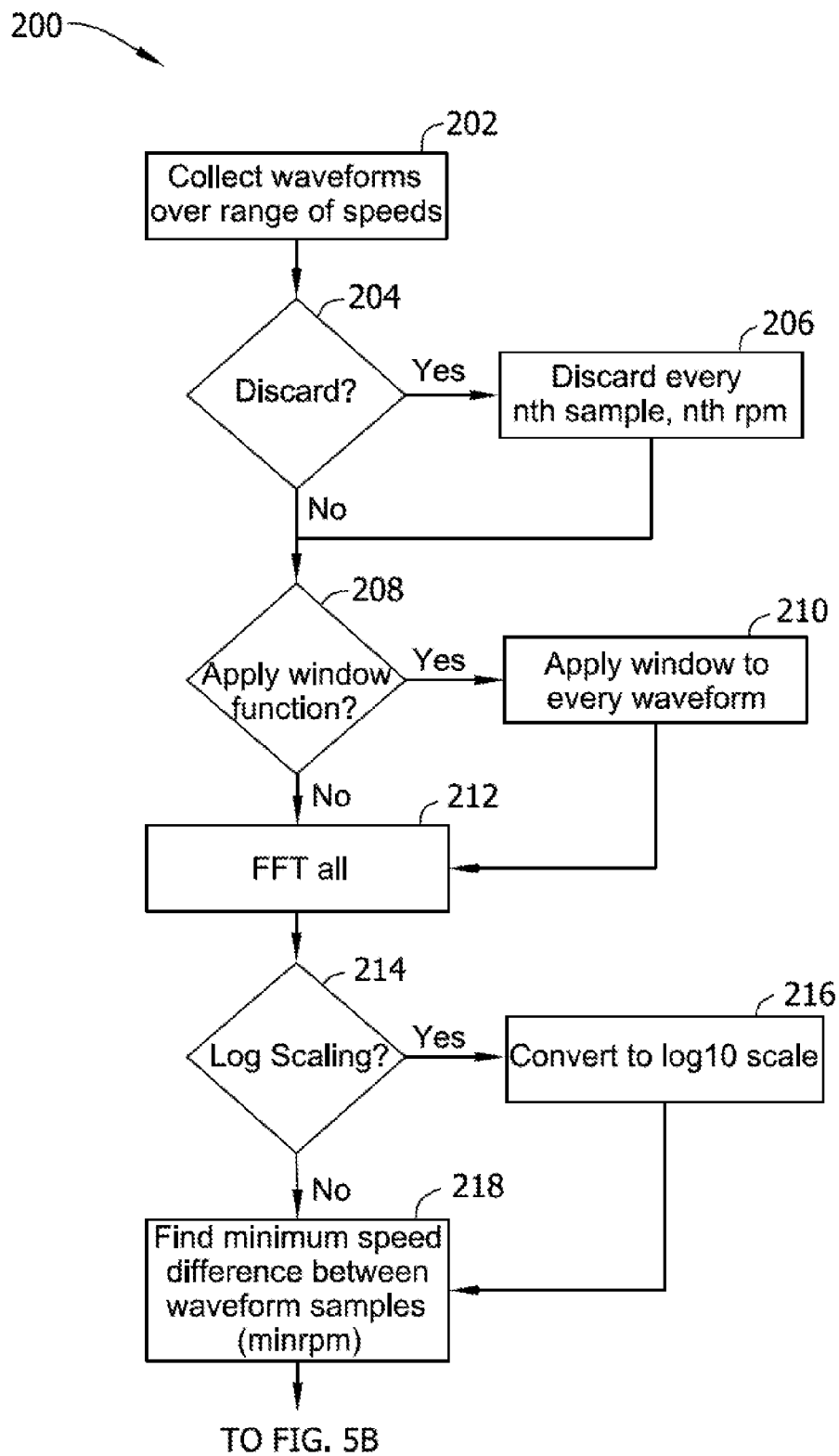
FIGS. 5A-5C collectively form a flowchart illustrating an exemplary method for generating an exemplary Campbell diagram display.
Figure 5B:
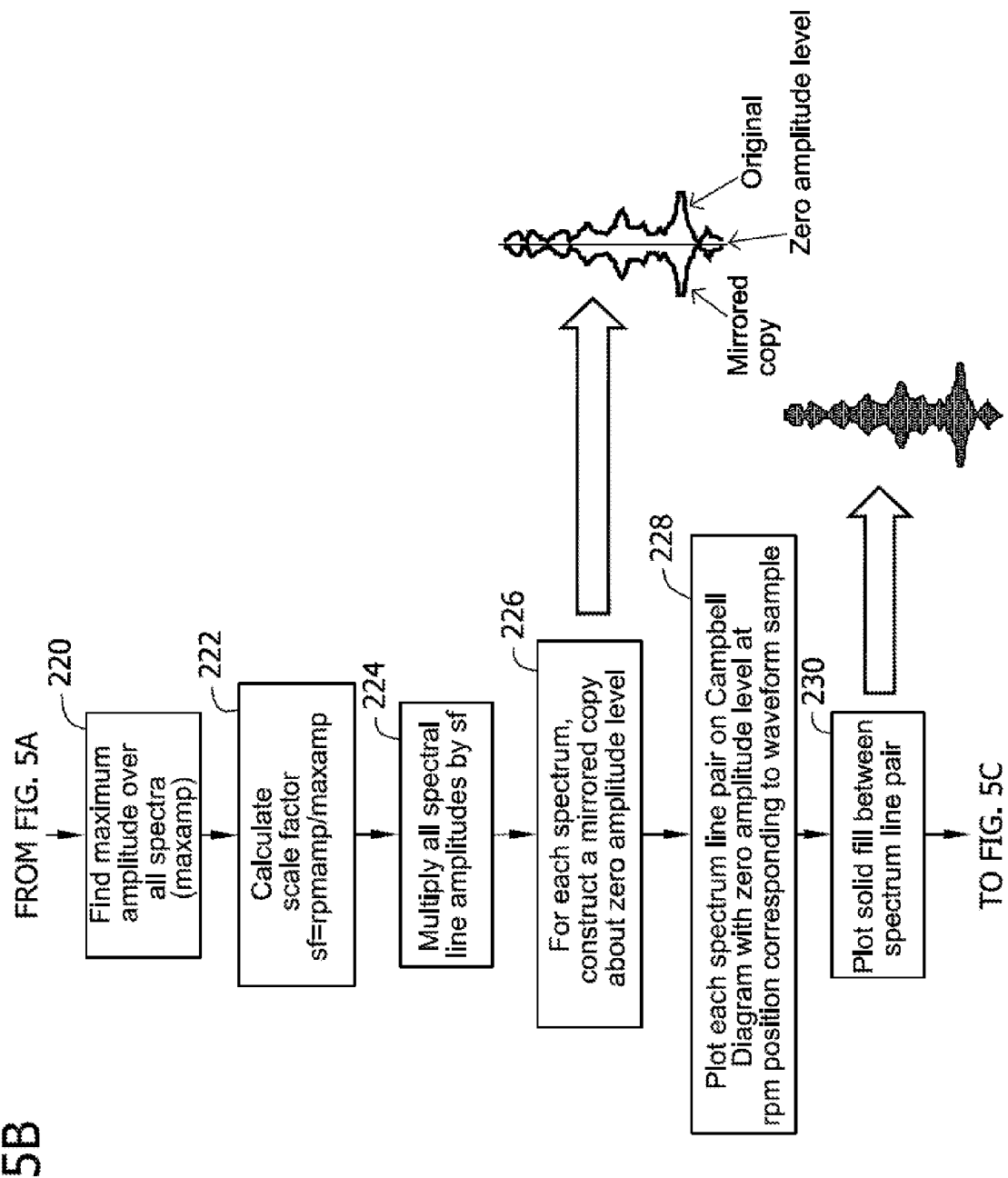
Figure 5C:
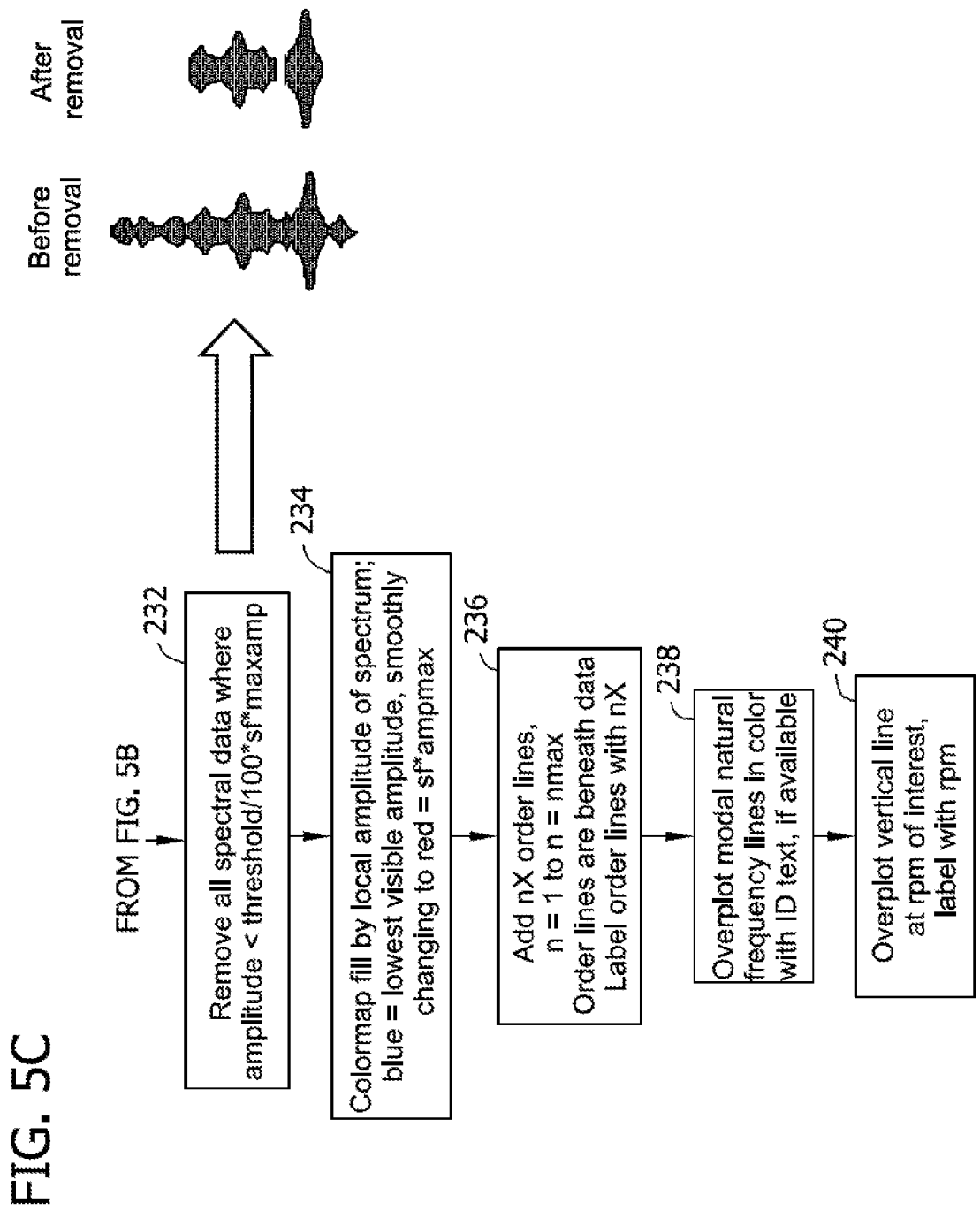

FIGS. 5A-5C collectively form a flow chart illustrating method 200 for sensing vibrations in apparatus 101 of system 100. One or more users affix sensors 102 (such as vibration sensing voltage transducers) to apparatus 101 and otherwise making all necessary connections for system 100. Method 200 begins with collection 202 of test data over a range of operating speeds, which data comprises a set or sets of data points that represent(s) a time-varying dynamic voltage signal(s), or waveforms, from the transducers. Sampling of sensor data may be taken stepwise with increasing/decreasing rotational speed, such as at 10 rpm intervals, or some other interval. As an optional aspect, system 100 may be suitably configured (programmed) to discard sampled data at predefined intervals, such as every $2^{nd}$ sample, every $3^{rd}$ sample, every $10^{th}$ sample, etc., and/or at predefined rpm intervals. Upon entry of the sensor data, system 100 determines 204 whether data discard has been selected. If data discard has been selected, system 100 discards 206 data according to a predefined one or more of the criteria described above.

After data has been discarded 206 according to the predefined criteria, or if no data discard has been selected, system 100 then determines 208 whether or not window functions are to be applied. "Window functions" refers to standardized conventional methods for processing waveforms, for example, by flattening the endpoints of a run of data to zero, by interpolating consecutive runs of data to ensure that the endpoints of the runs of data merge smoothly, etc. Such data processing techniques are well known to those of skill in the art. If system 100 has been so configured, system 100 applies 210 the window function to each collected waveform. Once processed in that manner, or if system 100 is configured not to apply the window function, system 100 performs 212 a fast Fourier transform operation ("FFT") to each waveform, which operates to calculate the frequency content in a signal. System 100 then determines 214 what form of scaling of the resulting processed spectral lines has been selected by the user (log or linear). If 216 log scaling was selected by the user, system 100 converts the spectral lines to logarithmic scaling, before further processing occurs. After scaling, or if no scaling was selected, system 100 determines 218 the minimum speed (RPM) difference between consecutive waveform data samples, determines 220 the maximum spectral amplitude over all spectra (maxamp); and calculates 222 the scale factor so that the spectral lines can be appropriately displayed on display 130. The scale factor is calculated as being equal to the maximum overall spectral amplitude, maxamp, divided by a maximum rpm scaling value, rpmamp. A default value for rpmamp can be used (for example 100 rpm), or maxamp can be user configurable. When scaled, the maximum overall spectral amplitude will cover a horizontal range of rpmamp rpm on the plot. System 100 then multiples 224 all the spectral lines derived from the collected waveform data by the scale factor (so that the units of spectral amplitude are in RPM), and constructs 226 a mirrored copy of the spectral lines about their respective zero amplitude lines to create spectral line pairs or spectral envelopes.

System 100 then plots 228 each spectral line pair on a Campbell diagram (see, e.g., diagram 132 on display 130, shown in FIG. 4), with the zero amplitude line situated at the RPM position corresponding to the particular waveform data sample to create spectral line pairs (or envelopes) 134, and plots 230 a solid fill between the spectral line pairs (inside the spectral envelopes) to create a solid profile. For purposes of the present description, "solid" refers to filling an area defined by a line with color or colors, stippling, shading, or any other illustrative feature capable of imparting an impression of solidity or continuity to the area bounded by the mirrored spectral lines.

System 100, if configured to do so and the user so elects, then removes 232 all spectral data where the amplitude of the waveform is less than a threshold value selected by the user (e.g., 0<threshold<95) divided by (100×scale factor×maximum amplitude, determined at 220). This step facilitates the removal of background noise and clarifies and emphasizes the resulting spectral line plots. System 100 may be configured to provide the user an option to colorize 234 the fill of the waveform plots by local amplitude, e.g., by employing blue to indicate the lowest visible amplitude, shifting to red for the maximum amplitude. System 100 then 236 adds nX order lines from n equals 1 to n equals $n_{max}$, being an integer selectable by the user between 0 and some maximum value, e.g., 20, with a default value of 10, but any desired default value can be used. System 100 plots the order lines to appear "beneath" the spectral envelope plots, and labels the order lines with appropriate designations. System 100 then 238 plots modal natural frequency lines (from data supplied by the user) in contrasting color(s) over the spectral envelopes 134, and applies suitable identifying text if desired and available. System 100 completes exemplary Campbell diagram 132 by overplotting 240 a vertical line 139 (e.g., in a contrasting color, such as red, line 139 shown in FIG. 4) at the RPM of interest, labeling vertical line 139 with the numerical value of a user-selected RPM of interest, or the actual operating speed of apparatus 101.

Figure 6:
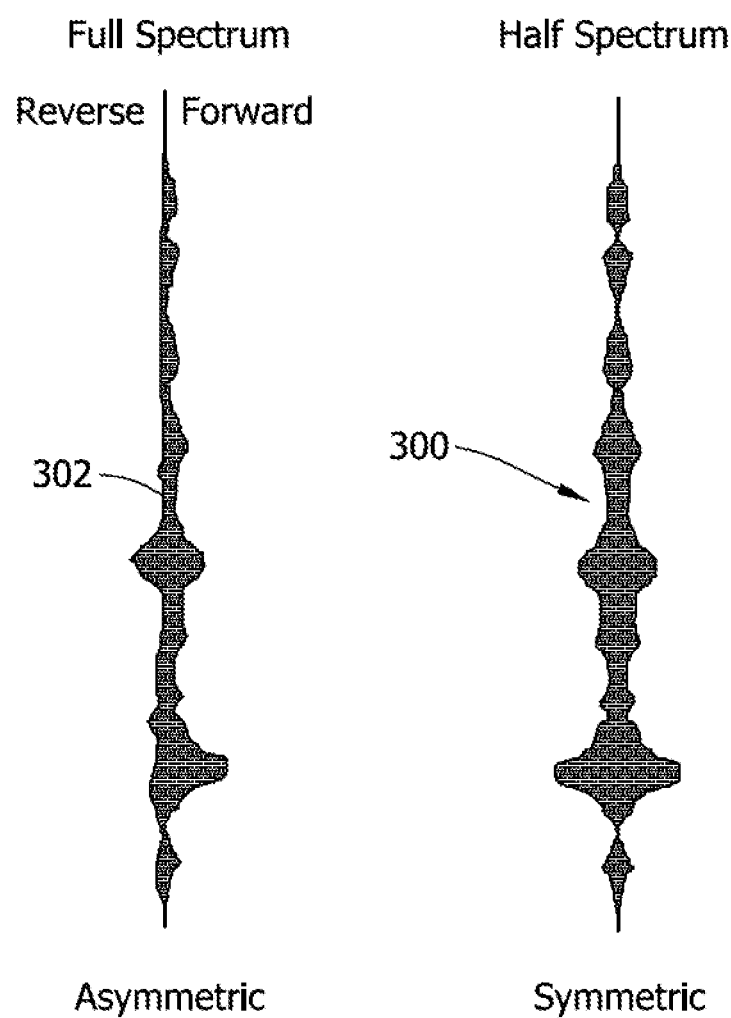
FIG. 6 is a side-by-side illustration of exemplary half and full spectrum Campbell diagram spectral envelope plots.

Exemplary Campbell diagram 132 and corresponding method 200 have been described with respect to a half-spectrum plot (also called a conventional spectrum, or the spectrum of a single signal) of vibration amplitude and frequency for an apparatus. In another exemplary embodiment, system 100 is configured to provide spectra for both forward and reverse vibration frequencies, where forward frequencies represent 2-dimensional vibration in the same angular sense as the direction of rotation of the machine rotor, and reverse frequencies represent vibration in the opposite angular sense as the direction of rotation of the machine rotor. FIG. 6 is a side-by-side illustration of exemplary half spectrum 300 and full spectrum 302 Campbell diagram spectral envelope plots. In an exemplary embodiment, system 100 is configured to fill the forward and reverse portions of full spectrum plot 302 with contrasting colors, or using other display techniques to ensure the user's ability to discern between the forward and reverse portions of the waveform plot.

Figure 7:
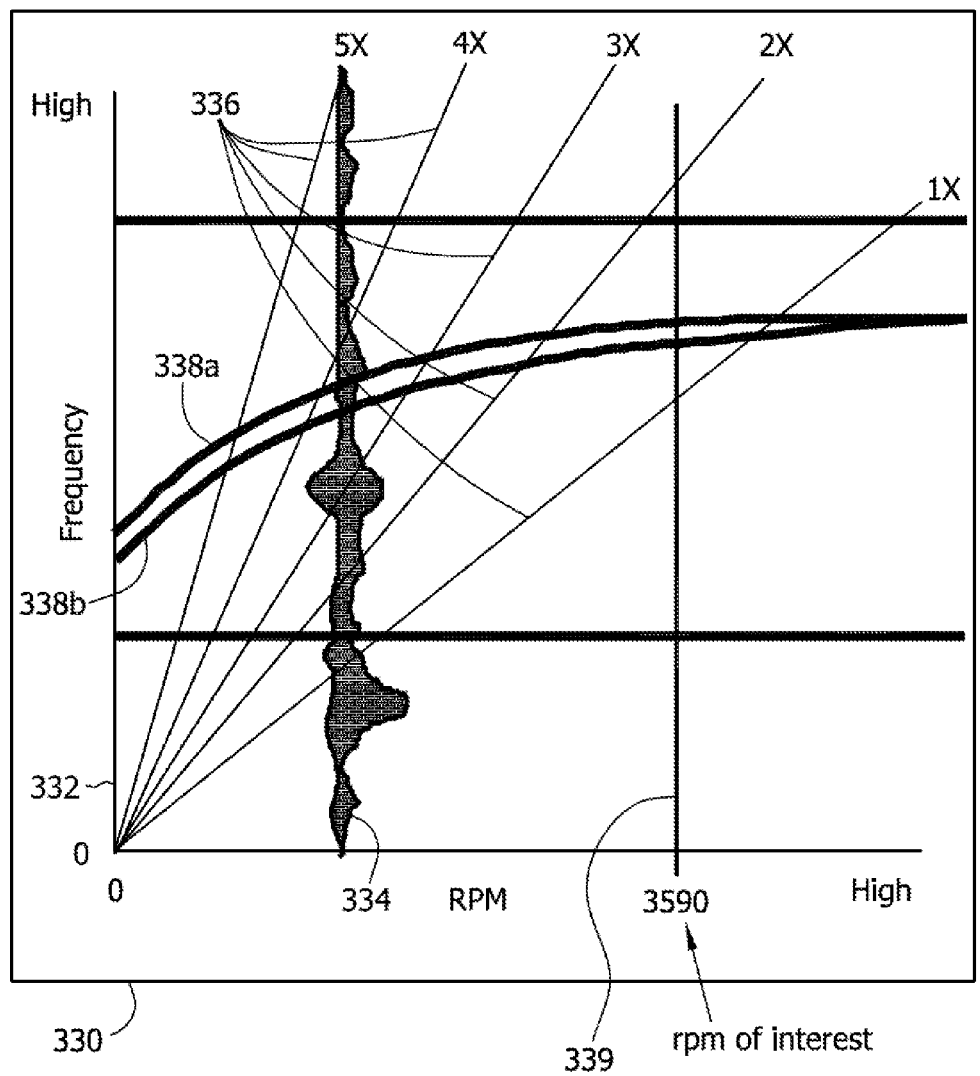
FIG. 7 illustrates an exemplary Campbell diagram display for a full spectrum spectral envelope.

FIG. 7 illustrates an exemplary Campbell diagram display 330 for a full spectrum spectral envelope. Diagram 332 includes full spectrum spectral envelope 334, together with order lines 336, RPM of interest line 339, and forward 338a and reverse 338b modal natural frequency lines, which may be illustrated in different colors, different line styles, or any other suitable way to enable a user to differentiate between the lines. In an exemplary embodiment, forward line 338a is plotted over reverse line 338b. In addition, the forward and reverse natural frequency lines 338a, 338b may be colored or otherwise depicted to correspond to the mode of illustration of the forward and reverse portions of the spectral envelope plot 334.

Figure 8:
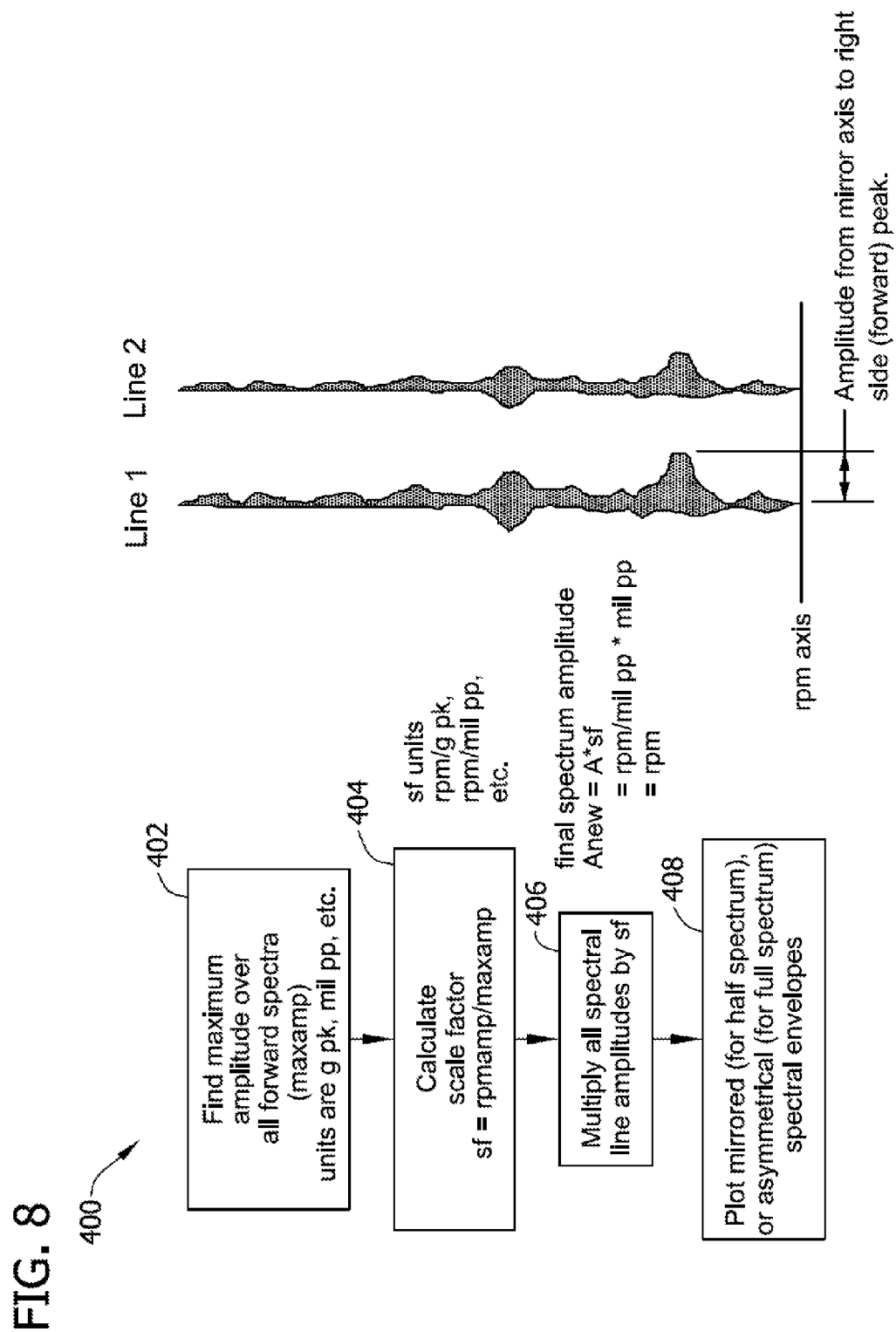
FIG. 8 is a partial flow chart for an alternative exemplary procedure for scaling exemplary Campbell diagram displays.

FIG. 8 is a partial flow chart for an alternative exemplary procedure for scaling exemplary Campbell diagram displays, which is an expansion of the procedure shown and described with respect to FIG. 5B. In submethod 400, which is suited for illustration of forward and reverse spectral envelopes in an exemplary Campbell diagram 334, system 100 is configured to determine 402 the maximum vibration amplitude (maxamp) over all the recorded forward vibration spectra from the collected data. As previously discussed, maxamp is the largest amplitude peak recorded in an entire multi-spectrum data set, for a particular testing session. System 100 then calculates 404 the scale factor, which equals RPMamp divided by maxamp, wherein RPMamp is a user-selectable factor between 1 and 10,000, and having a default value, e.g., of 100. System 100 then 406 multiplies all spectral lines by the just calculated scale factor, and plots 408 a mirrored spectral line pair (for a half-spectrum plot) or an asymmetrical plot for a full spectrum spectral envelope. In an exemplary embodiment, if the default RPMamp value of 100 is employed, the largest magnitude amplitude on the forward frequency (right) side of a spectral envelope plot will be 100 RPM on that plot, with all other amplitudes being less.

In an exemplary system 100, Campbell diagram 132 will be generated, after a complete test run of a rotating machine, such as turbine, has been accomplished, either during run-up or run-down, of the machine. In an alternative exemplary system 100, system 100 is configured to generate a Campbell diagram display real-time, of a single spectral envelope at a constant rotational speed, being the steady-state RPM of the rotating machine at that time.

The above-described embodiments provide methods and systems for more effectively displaying an increased amount of information in Campbell diagram displays, as compared to known Campbell diagram displays. For example, the filled envelopes representing either half- or full-spectrum spectral lines provides an improved and more prominent indication of the rotational speeds at which excessive vibrations are encountered, without having to provide specific numerical data in the display. In addition, for full spectrum spectral envelopes, the differences between forward and reverse frequencies are visually emphasized and more readily distinguished from one another.

Exemplary embodiments of Campbell diagram displays and methods of implementing same are described above in detail. The apparatus, method and system are not limited to the specific embodiments described herein, but rather, components of the apparatus and/or system and/or steps of the method may be utilized independently and separately from other components and/or steps described herein. For example, the Campbell diagram display system may also be used in combination with other measurement systems and methods, and is not limited to practice with systems for measurement of vibrations as described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for indicating characteristics of a moving apparatus in the form of a Campbell diagram, comprising:
   receiving, from a sensor and at a processor, control apparatus waveform data corresponding to amplitudes and frequencies of vibrations of the apparatus at each of a plurality of rotational speeds;
   processing, by the processor, the amplitude and vibration waveform data to create at least one spectral line representing the received amplitudes and frequencies of the vibrations of the apparatus corresponding to a predefined rotational speed of the apparatus;

generating, using the processor, a spectral line envelope from the at least one spectral line by mirroring the at least one spectral line about a zero amplitude line, wherein the spectral line envelope represents vibration characteristics over a period of time and a range of rotational speeds, and represents real-time vibration characteristics for a current rotational speed of a rotary machine;

plotting, using the processor, the spectral line envelope into a Campbell diagram representing rotational vibration characteristics for the apparatus by positioning the spectral line envelope so that the zero amplitude line extends perpendicular to an RPM axis of the Campbell diagram, at a location corresponding to the predefined rotational speed of interest; and filling, using the processor, the spectral line envelope to create a visually solid two-dimensional image representative of amplitudes of vibration of the apparatus across a range of vibration frequencies at the predefined rotational speed of the apparatus.

2. The method of claim 1, comprising:
creating, using the processor, an image of the Campbell diagram incorporating the filled spectral line envelope; and
displaying the image of the Campbell diagram on a display apparatus.

3. The method of claim 1, comprising:
filtering, using the processor, the data to remove data points corresponding to predefined criteria.

4. The method of claim 3, wherein filtering the data to remove data points corresponding to predefined criteria comprises at least one of:
removing data points measured by the sensor at predefined sampling intervals; and
removing data points measured by the sensor at predefined rotational speed intervals.

5. The method of claim 1, comprising:
displaying a plurality of filled waveform envelopes representing a plurality of data sets corresponding to a plurality of rotational speeds of interest.

6. The method of claim , comprising:
horizontally scaling each spectral line.

7. The method of claim 1, wherein filling the spectral line envelope to create a visually solid two-dimensional image representative of amplitudes of vibration of the apparatus across a range of vibration frequencies at the predefined rotational speed of the apparatus comprises one of:
filling the spectral line envelope with a single continuous color; and
filling the spectral line envelope with a smoothly transitioning color according to a magnitude of the amplitude of vibration being depicted.

8. The method of claim 1, wherein the at least one spectral line comprises a forward frequency spectral line and a reverse frequency spectral line; and
generating a spectral line envelope from the at least one spectral line comprises plotting the forward and reverse spectral lines on opposite sides of the zero amplitude line.

9. A system for displaying characteristics of a moving apparatus in the form of a Campbell diagram, comprising:
a control apparatus comprising:
a processor;
memory storing instructions configured to cause the processor to:
receive, from a sensor, waveform data corresponding to amplitudes and frequencies of vibrations of the apparatus at each of a plurality of rotational speeds;
process the amplitude and vibration waveform data to create at least one spectral line representing the received amplitudes and frequencies of the vibrations of the apparatus corresponding to a predefined rotational speed of the apparatus;
generate a spectral line envelope from the at least one spectral line by mirroring the at least one spectral line about a zero amplitude line, wherein the spectral line envelope represents vibration characteristics over a period of time and a range of rotational speeds, and represents real-time vibration characteristics for a current rotational speed of a rotary machine;
plot the spectral line envelope into a Campbell diagram representing rotational vibration characteristics for the apparatus by positioning the spectral line envelope so that the zero amplitude line extends perpendicular to an RPM axis of the Campbell diagram, at a location corresponding to the predefined rotational speed of interest; and
fill the spectral line envelope to create a visually solid two-dimensional image representative of amplitudes of vibration of the apparatus across a range of vibration frequencies at the predefined rotational speed of the apparatus; and
a display apparatus configured to display the image of the Campbell diagram.

10. The system of claim 9, wherein the instructions are configured to cause the processor to filter the data to remove data points corresponding to predefined criteria.

11. The system of claim 10, wherein the instructions are configured to cause the processor to perform at least one of:
remove data points measured by the sensor at predefined sampling intervals; and
remove data points measured by the sensor at predefined rotational speed intervals.

12. The system of claim 9, wherein the display apparatus is configured to:
display a plurality of filled spectral line envelopes representing a plurality of data sets corresponding to a plurality of rotational speeds of interest.

13. The system of claim 12, wherein the instructions are configured to cause the processor to horizontally scale each spectral line.

14. The system of claim 9, wherein the instructions are configured to cause the processor to perform one of:
fill the spectral line envelope with a single continuous color; and
fill the waveform envelope with a smoothly transitioning color according to a magnitude of the amplitude of vibration being depicted.

15. The system of claim 9, wherein the at least one spectral line comprises a forward frequency spectral line and a reverse frequency spectral line; and the instructions are configured to cause the processor to generate a spectral line envelope from the at least one spectral line comprises plotting the forward and reverse spectral lines on opposite sides of a zero amplitude line.

* * * * *